(12) United States Patent
Snyder

(10) Patent No.: US 11,752,331 B2
(45) Date of Patent: Sep. 12, 2023

(54) NERVE CUFF DEPLOYMENT DEVICES

(71) Applicant: Neuros Medical, Inc., Willoughby Hills, OH (US)

(72) Inventor: Jon Joseph Snyder, Kirtland, OH (US)

(73) Assignee: Neuros Medical, Inc., Aliso Viejo, CA (US)

( * ) Notice: Subject to any disclaimer, the term of this patent is extended or adjusted under 35 U.S.C. 154(b) by 98 days.

(21) Appl. No.: 17/444,876

(22) Filed: Aug. 11, 2021

(65) Prior Publication Data
US 2021/0370054 A1 Dec. 2, 2021

Related U.S. Application Data

(63) Continuation of application No. 16/954,049, filed as application No. PCT/US2018/065447 on Dec. 13, 2018, now Pat. No. 11,116,965.

(60) Provisional application No. 62/598,369, filed on Dec. 13, 2017.

(51) Int. Cl.
*A61N 1/36* (2006.01)
*A61N 1/05* (2006.01)
*A61B 17/34* (2006.01)
*A61F 2/72* (2006.01)

(52) U.S. Cl.
CPC ........ *A61N 1/0556* (2013.01); *A61B 17/3468* (2013.01); *A61F 2/72* (2013.01)

(58) Field of Classification Search
CPC .. A61N 1/0556; A61N 1/0558; A61N 1/0551; A61B 17/3468
See application file for complete search history.

(56) References Cited

U.S. PATENT DOCUMENTS

| | | |
|---|---|---|
| 3,738,368 A | 6/1973 | Avery et al. |
| 4,155,366 A | 5/1979 | Di Mucci |
| 4,573,481 A | 3/1986 | Bullara |
| 4,602,624 A | 7/1986 | Naples et al. |
| 4,979,511 A | 12/1990 | Terry |
| 5,143,067 A | 9/1992 | Rise et al. |
| 5,324,322 A | 6/1994 | Grill et al. |
| 5,653,739 A | 8/1997 | Maurer et al. |
| 5,755,750 A | 5/1998 | Petruska et al. |
| 5,964,702 A | 10/1999 | Grill, Jr. et al. |
| 6,058,331 A | 5/2000 | King |
| 6,275,735 B1 | 8/2001 | Jarding et al. |
| 6,292,703 B1 | 9/2001 | Meier et al. |
| 6,456,866 B1 | 9/2002 | Tyler et al. |

(Continued)

FOREIGN PATENT DOCUMENTS

| | | |
|---|---|---|
| CN | 102573986 A | 7/2012 |
| DE | 202010015346 U1 | 4/2011 |

(Continued)

OTHER PUBLICATIONS

Ackermann et al.; Effect of bipolar cuff electrode design on block thresholds in high-frequency electrical neural conduction block; IEEE Transactions on Neural Systems and Rehabilitation Engineering; 17(5); pp. 469-477; Oct. 1, 2009.

(Continued)

*Primary Examiner* — Jon Eric C Morales
(74) *Attorney, Agent, or Firm* — Shay Glenn LLP

(57) ABSTRACT

Nerve cuff deployment apparatuses and methods of using them to deliver a nerve cuff electrode to a target nerve trunk.

20 Claims, 10 Drawing Sheets

(56) References Cited

U.S. PATENT DOCUMENTS

| | | |
|---|---|---|
| 6,699,275 B1 | 3/2004 | Knudson et al. |
| 6,735,475 B1 | 5/2004 | Whitehurst et al. |
| 6,760,626 B1 | 7/2004 | Boveja |
| 6,836,685 B1 | 12/2004 | Fitz |
| 6,860,851 B2 | 3/2005 | Knudson et al. |
| 6,871,099 B1 | 3/2005 | Whitehurst et al. |
| 7,076,307 B2 | 7/2006 | Boveja et al. |
| 7,167,750 B2 | 1/2007 | Knudson et al. |
| 7,201,757 B2 | 4/2007 | Knudson et al. |
| 7,292,890 B2 | 11/2007 | Whitehurst et al. |
| 7,295,876 B1 | 11/2007 | Erickson |
| 7,302,296 B1 | 11/2007 | Hoffer |
| 7,324,852 B2 | 1/2008 | Barolat et al. |
| 7,389,145 B2 | 6/2008 | Kilgore et al. |
| 7,444,183 B2 | 10/2008 | Knudson et al. |
| 7,463,927 B1 | 12/2008 | Chaouat |
| 7,489,966 B2 | 2/2009 | Leinders et al. |
| 7,555,345 B2 | 6/2009 | Wahlstrand et al. |
| 7,616,990 B2 | 11/2009 | Chavan et al. |
| 7,761,166 B2 | 7/2010 | Giftakis et al. |
| 7,839,415 B2 | 11/2010 | Hillard et al. |
| 7,860,570 B2 | 12/2010 | Whitehurst et al. |
| 7,894,905 B2 | 2/2011 | Pless et al. |
| 7,894,906 B2 | 2/2011 | Shuros |
| 7,979,131 B2 | 7/2011 | Feler et al. |
| 8,027,718 B2 | 9/2011 | Spinner et al. |
| 8,060,208 B2 | 11/2011 | Kilgore et al. |
| 8,060,209 B2 | 11/2011 | Jaax et al. |
| 8,108,052 B2 | 1/2012 | Boling |
| 8,116,882 B2 | 2/2012 | Kowalczewski |
| 8,170,675 B2 | 5/2012 | Alataris et al. |
| 8,185,207 B2 | 5/2012 | Molnar et al. |
| 8,219,202 B2 | 7/2012 | Giftakis et al. |
| 8,224,453 B2 | 7/2012 | De Ridder |
| 8,380,318 B2 | 2/2013 | Kishawi et al. |
| 8,452,417 B2 | 5/2013 | Navarro |
| 8,467,879 B1 | 6/2013 | Whitehurst et al. |
| 8,498,711 B2 | 7/2013 | Roche |
| 8,504,147 B2 | 8/2013 | Deem et al. |
| 8,521,291 B1 | 8/2013 | Cholette et al. |
| 8,560,075 B2 | 10/2013 | Covalin |
| 8,594,796 B2 | 11/2013 | Roche |
| 8,600,505 B2 | 12/2013 | Libbus et al. |
| 8,676,329 B2 | 3/2014 | Wacnik et al. |
| 8,676,331 B2 | 3/2014 | Parker |
| 8,712,547 B2 | 4/2014 | Whitehurst et al. |
| 8,731,676 B2 | 5/2014 | Fang et al. |
| 8,738,140 B2 | 5/2014 | De Ridder |
| 8,755,893 B2 | 6/2014 | Gross et al. |
| 8,761,892 B2 | 6/2014 | Weisgarber et al. |
| 8,788,045 B2 | 7/2014 | Gross et al. |
| 8,805,518 B2 | 8/2014 | King et al. |
| 8,903,502 B2 | 12/2014 | Perryman et al. |
| 8,923,975 B2 | 12/2014 | Bradley |
| 8,965,516 B2 | 2/2015 | Bennett et al. |
| 8,977,362 B2 | 3/2015 | Saab |
| 8,983,612 B2 | 3/2015 | Fang et al. |
| 8,983,614 B2 | 3/2015 | Kilgore et al. |
| 9,031,658 B2 | 5/2015 | Chiao et al. |
| 9,037,248 B2 | 5/2015 | Durand et al. |
| 9,089,700 B2 | 7/2015 | Hlavka et al. |
| 9,095,699 B2 | 8/2015 | Rosenberg et al. |
| 9,132,272 B2 | 9/2015 | Alves et al. |
| 9,259,575 B2 | 2/2016 | Zhao et al. |
| 9,295,840 B1 | 3/2016 | Thacker et al. |
| 9,295,841 B2 | 3/2016 | Fang et al. |
| 9,327,121 B2 | 5/2016 | Thacker et al. |
| 9,339,655 B2 | 5/2016 | Carbunaru |
| 9,387,325 B1 | 7/2016 | Min et al. |
| 9,403,008 B2 | 8/2016 | Howard |
| 9,403,014 B2 | 8/2016 | Kilgore et al. |
| 9,409,019 B2 | 8/2016 | Walker et al. |
| 9,421,372 B2 | 8/2016 | Mashiach et al. |
| 9,604,062 B2 | 3/2017 | Carroll |
| 9,630,011 B2 | 4/2017 | Lipani |
| 9,694,181 B2 | 7/2017 | Bhadra et al. |
| 9,814,881 B2 | 11/2017 | Moffitt |
| 9,884,189 B2 | 2/2018 | Boggs |
| 9,884,192 B2 | 2/2018 | Kilgore et al. |
| 9,889,293 B2 | 2/2018 | Siegel et al. |
| 9,931,510 B2 | 4/2018 | Hou et al. |
| 9,937,348 B1 | 4/2018 | Bradley |
| 9,956,398 B2 | 5/2018 | Callegari et al. |
| 10,086,201 B2 | 10/2018 | Chang et al. |
| 10,105,541 B2 | 10/2018 | Kishawi et al. |
| 10,149,978 B1 | 12/2018 | Park |
| 10,159,838 B2 | 12/2018 | Kim et al. |
| 10,195,434 B2 | 2/2019 | Bhadra et al. |
| 10,238,872 B2 | 3/2019 | Pivonka et al. |
| 10,258,805 B2 | 4/2019 | Reed et al. |
| 10,286,213 B2 | 5/2019 | Fletcher et al. |
| 10,300,273 B2 | 5/2019 | Rooney et al. |
| 10,315,034 B2 | 6/2019 | Hou et al. |
| 10,328,256 B1 | 6/2019 | Gliner |
| 10,390,877 B2 | 8/2019 | Heggeness et al. |
| 10,456,575 B2 | 10/2019 | Kilgore et al. |
| 10,617,870 B2 | 4/2020 | Kilgore et al. |
| 10,632,309 B2 | 4/2020 | McGee et al. |
| 10,675,469 B2 | 6/2020 | Annoni et al. |
| 10,722,703 B2 | 7/2020 | Mitchell |
| 10,758,723 B2 | 9/2020 | Fang et al. |
| 10,780,270 B2 | 9/2020 | Schepis et al. |
| 10,799,701 B2 | 10/2020 | Lee |
| 10,828,491 B2 | 11/2020 | Schepis et al. |
| 10,864,373 B2 | 12/2020 | Bhadra et al. |
| 10,894,159 B2 | 1/2021 | De Ridder |
| 10,926,092 B2 | 2/2021 | Esteller et al. |
| 10,953,228 B2 | 3/2021 | Perryman et al. |
| 10,967,183 B2 | 4/2021 | Yakovlev et al. |
| 11,007,364 B2 | 5/2021 | Carroll |
| 11,027,126 B2 | 6/2021 | Ackermann et al. |
| 11,071,863 B2 | 7/2021 | Torgerson |
| 11,116,965 B2 | 9/2021 | Snyder |
| 11,116,975 B2 | 9/2021 | Oron et al. |
| 11,167,129 B2 | 11/2021 | Parker |
| 11,235,146 B2 | 2/2022 | Boggs et al. |
| 11,247,053 B2 | 2/2022 | Rajguru et al. |
| 11,253,705 B1 | 2/2022 | John |
| 11,278,718 B2 | 3/2022 | Faltys et al. |
| 11,311,726 B2 | 4/2022 | Vansickle et al. |
| 11,331,489 B2 | 5/2022 | Johanek |
| 11,331,493 B2 | 5/2022 | Pivonka et al. |
| 11,344,726 B2 | 5/2022 | Bennett et al. |
| 11,344,729 B1 | 5/2022 | Single et al. |
| 2002/0055779 A1 | 5/2002 | Andrews |
| 2002/0198572 A1 | 12/2002 | Weiner |
| 2003/0144709 A1 | 7/2003 | Zabara et al. |
| 2004/0015295 A1 | 1/2004 | Whitehurst et al. |
| 2004/0111139 A1 | 6/2004 | McCreery |
| 2004/0147977 A1 | 7/2004 | Petrofsky |
| 2004/0243182 A1 | 12/2004 | Cohen et al. |
| 2005/0131485 A1 | 6/2005 | Knudson et al. |
| 2005/0137648 A1 | 6/2005 | Cosendai et al. |
| 2005/0143789 A1 | 6/2005 | Whitehurst et al. |
| 2005/0149148 A1 | 7/2005 | King |
| 2005/0149154 A1 | 7/2005 | Cohen et al. |
| 2006/0025832 A1 | 2/2006 | O'Keeffe et al. |
| 2006/0030919 A1 | 2/2006 | Mrva et al. |
| 2006/0184211 A1 | 8/2006 | Gaunt et al. |
| 2006/0195158 A1 | 8/2006 | Cory |
| 2006/0270944 A1 | 11/2006 | King et al. |
| 2006/0271137 A1 | 11/2006 | Stanton-Hicks |
| 2006/0293721 A1 | 12/2006 | Tarver et al. |
| 2007/0043400 A1 | 2/2007 | Donders |
| 2007/0142863 A1 | 6/2007 | Bradley |
| 2007/0185549 A1 | 8/2007 | Zdeblick |
| 2008/0027505 A1 | 1/2008 | Levin et al. |
| 2008/0046055 A1 | 2/2008 | Durand et al. |
| 2008/0086180 A1 | 4/2008 | Ben-Ezra et al. |
| 2008/0172116 A1* | 7/2008 | Mrva ............... A61N 1/0526 607/115 |
| 2008/0183226 A1 | 7/2008 | Buras et al. |
| 2008/0228194 A1* | 9/2008 | Westlund ............ A61N 1/0556 607/2 |

(56) References Cited

U.S. PATENT DOCUMENTS

| | | |
|---|---|---|
| 2008/0319511 A1 | 12/2008 | Pless |
| 2009/0069738 A1 | 3/2009 | Rossing et al. |
| 2009/0083070 A1 | 3/2009 | Giftakis et al. |
| 2009/0204173 A1 | 8/2009 | Fang et al. |
| 2009/0281595 A1 | 11/2009 | King et al. |
| 2010/0121408 A1 | 5/2010 | Imran et al. |
| 2010/0152808 A1 | 6/2010 | Boggs, II |
| 2010/0168820 A1 | 7/2010 | Maniak et al. |
| 2010/0211135 A1 | 8/2010 | Caparso et al. |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274316 A1 | 10/2010 | Alataris et al. |
| 2010/0274317 A1 | 10/2010 | Parker et al. |
| 2010/0274318 A1 | 10/2010 | Walker et al. |
| 2010/0274326 A1 | 10/2010 | Chitre et al. |
| 2011/0071593 A1 | 3/2011 | Parker et al. |
| 2011/0230701 A1 | 9/2011 | Simon et al. |
| 2012/0016439 A1 | 1/2012 | Alataris et al. |
| 2012/0083709 A1 | 4/2012 | Parker et al. |
| 2012/0083856 A1 | 4/2012 | Thacker et al. |
| 2012/0089199 A1 | 4/2012 | Bolea et al. |
| 2012/0232615 A1 | 9/2012 | Barolat et al. |
| 2012/0253261 A1 | 10/2012 | Poletto et al. |
| 2013/0035735 A1 | 2/2013 | Kroll |
| 2013/0289664 A1 | 10/2013 | Johanek |
| 2013/0289667 A1 | 10/2013 | Wacnik et al. |
| 2014/0046398 A1 | 2/2014 | Sachs et al. |
| 2014/0188186 A1 | 7/2014 | Barolat et al. |
| 2014/0228905 A1 | 8/2014 | Bolea |
| 2015/0230809 A1* | 8/2015 | Becker .............. A61B 1/00135 600/115 |
| 2016/0256685 A1 | 9/2016 | Haessler |
| 2016/0361542 A1 | 12/2016 | Kaula et al. |
| 2017/0007836 A1 | 1/2017 | Nassif |
| 2017/0095667 A1 | 4/2017 | Yakovlev et al. |
| 2017/0239486 A1 | 8/2017 | Suryavanshi |
| 2017/0319381 A1 | 11/2017 | Rogers |
| 2017/0333701 A1 | 11/2017 | Bradley et al. |
| 2017/0348532 A1 | 12/2017 | Moffitt et al. |
| 2018/0008827 A1 | 1/2018 | Dolev et al. |
| 2018/0021577 A1 | 1/2018 | Phillips |
| 2018/0043172 A1 | 2/2018 | Serrano Carmona |
| 2018/0056066 A1 | 3/2018 | Boggs et al. |
| 2018/0140835 A1 | 5/2018 | Sharma |
| 2018/0333576 A1 | 11/2018 | Rigaux |
| 2019/0151659 A1 | 5/2019 | Mishra et al. |
| 2019/0184170 A1 | 6/2019 | Knudson et al. |
| 2019/0308020 A1 | 10/2019 | Syed Shah et al. |
| 2019/0358455 A1 | 11/2019 | Lin et al. |
| 2019/0358466 A1 | 11/2019 | Leung et al. |
| 2019/0374779 A1 | 12/2019 | Kilgore et al. |
| 2020/0391032 A1 | 12/2020 | Fang et al. |
| 2021/0113840 A1 | 4/2021 | Bhadra et al. |
| 2021/0154478 A1 | 5/2021 | Hincapie Ordonez et al. |
| 2021/0220642 A1 | 7/2021 | Fang et al. |
| 2021/0236820 A1 | 8/2021 | Parker et al. |
| 2021/0244952 A1 | 8/2021 | Iorio et al. |
| 2021/0252288 A1 | 8/2021 | Lin et al. |
| 2021/0260381 A1 | 8/2021 | Kilgore et al. |
| 2021/0283398 A1 | 9/2021 | Kibler et al. |
| 2021/0283401 A1 | 9/2021 | Tai |
| 2021/0308456 A1 | 10/2021 | Gliner et al. |
| 2022/0008723 A1 | 1/2022 | Hsu et al. |
| 2022/0016421 A1 | 1/2022 | Boggs et al. |
| 2022/0023634 A1 | 1/2022 | Parker et al. |
| 2022/0023635 A1 | 1/2022 | Pepin et al. |
| 2022/0023648 A1 | 1/2022 | Doan et al. |
| 2022/0032060 A1 | 2/2022 | Bhadra et al. |
| 2022/0152393 A1 | 5/2022 | Kent et al. |
| 2022/0176108 A1 | 6/2022 | Linden et al. |
| 2022/0339446 A1 | 10/2022 | Fang et al. |

FOREIGN PATENT DOCUMENTS

| | | |
|---|---|---|
| EP | 3219357 A1 | 9/2017 |
| JP | 2009522015 A | 6/2009 |
| JP | 2012130579 A | 7/2012 |
| WO | WO00/61222 A1 | 10/2000 |
| WO | WO2005/105202 A1 | 11/2005 |
| WO | WO2007/117347 A1 | 10/2007 |
| WO | WO2009/079270 A1 | 6/2009 |
| WO | WO2012/159002 A8 | 11/2012 |
| WO | WO2018/033855 A1 | 2/2018 |
| WO | WO2018/067239 A1 | 4/2018 |
| WO | WO2018/106839 A2 | 6/2018 |
| WO | WO2020/041323 A1 | 2/2020 |

OTHER PUBLICATIONS

Ackermann et al.; Electrical conduction block in large nerves: high frequency current delivery in the nonhuman primate; Muscle and Nerve. 43(6); pp. 897-899; Jun. 2011.

Becker et al.; Essentials of local anesthetic pharmacology; Anesthesia progress; 53(3); pp. 98-109; Sep. 2006.

Bhadra et al.; High-frequency electrical conduction block of mammalian peripheral motor nerve; Muscle and Nerve; 32(6); pp. 782-790; Dec. 2005.

Bhadra et al.; Simulation of high-frequency sinusoidal electrical block of mammalian myelinated axons; Journal of Computational Neuroscience; 22(3); pp. 313-326; Jun. 1, 2007.

Bouaziz et al.; Neurologic complication of peripheral neural blockade. In Cousins and Bridenbaugh's Neural blockade in clinical anesthesia and pain medicine, 4th ed. (Cousins et al., eds.); Ch. 20; Lippincott Williams and Wilkins; pp. 464-477: (year of pub sufficiently earlier than effective US filing date and any foreign priority date) 2009.

Cleeland et al.; Pain assessment: global use of the Brief Pain Inventory; Annals, Academy of Medicine, Singapore; 23(2); pp. 129-138; Mar. 1994.

Dickinson et al.; Maldynia: pathophysiology and management of neuropathic and maladaptive pain'a report of the AMA Council on Science and Public Health; Pain Medicine; 11(11); pp. 1635-1653; Nov. 1, 2010.

Dworkin et al.; Interpreting the clinical importance of treatment outcomes in chronic pain clinical trials: IMMPACT recommendations; The Journal of Pain; 9(2); pp. 105-121; Feb. 1, 2008.

Fisher et al.; Chronic stability and selectivity of four-contact spiral nerve-cuff electrodes in stimulating the human femoral nerve; J. Neural Eng.; 6(4); pp. 1-16; Aug. 2009.

Flor et al.; Phantom limb pain: a case of maladaptive CNS plasticity? Nature Reviews Neuroscience; 7(11); pp. 873-881; Nov. 2006.

Fyfe, N.; An audit of amputation levels in patients referred for prosthetic rehabilitation; Prosthetics and Orthotics International; 14(2); pp. 67-70; Aug. 1990.

Gerges et al.; Frequency-and amplitude-transitioned waveforms mitigate the onset response in high-frequency nerve block; Journal of Neural Engineering; 7(6); pp. 1-17; Dec. 2010.

Guse et al.; Outcomes of the surgical treatment of peripheral neuromas of the hand and forearm: a 25-year comparative outcome study; Annals of plastic surgery; 71(6); pp. 654-658; (abstract) Dec. 1, 2013.

Hadzic et al.; Neurologic complications of peripheral nerve blocks. In Peripheral nerve blocks: principles and practice, 3rd ed. (Hadzic and Vloka, eds.); Ch. 6; New York: McGraw-Hill; pp. 67-77; Sep. 20, 2004.

Haroutounian et al.; Primary afferent input critical for maintaining spontaneous pain in peripheral neuropathy; Pain; 155(7); pp. 1272-1279 (abstract); Jul. 1, 2014.

Hsu et al.; Postamputation pain: epidemiology, mechanisms, and treatment; Journal of Pain Research; 6; pp. 121-136; Feb. 12, 2013.

Keller et al.; Validity of the brief pain inventory for use in documenting the outcomes of patients with noncancer pain; The Clinical Journal of Pain; 20(5); pp. 309-318; Sep. 1, 2004.

(56) References Cited

OTHER PUBLICATIONS

Kilgore et al.; Block of mammalian motor nerve conduction using high frequency alternating current; 10th Annual Conference of International FES Society; Montreal, Canada; pp. 479-481; Jul. 2005.

Kilgore et al.; Nerve conduction block utilizing high-frequency alternating current; Med. Biol. Eng. Comput.; 42(3); pp. 394-406; May 1, 2004.

Kilgore et al.; Reversible nerve conduction block using kilohertz frequency alternating current; Neuromodulation: Technology at the Neural Interface; 17(3); pp. 242-255; Apr. 2014.

Kumar et al.; Spinal cord stimulation versus conventional medical management for neuropathic pain: A multicentre randomised controlled trial in patients with failed back surgery syndrome; Pain; 132(1-2); pp. 179-188; Nov. 1, 2007.

Leland et al.; American war and military operations casualties: lists and statistics. Congressional Research Service; CRS Report to Congress; RL32492; pp. 1-30; Feb. 26, 2010.

Lewin-Kowalik et al.; Prevention and management of painful neuroma; Neurol Med Chir (Tokyo); 46(2); pp. 62-68; Feb. 2006.

Melzack et al.; Pain mechanisms: a new theory; Science; 150(3699); pp. 971-979; Nov. 19, 1965.

Miles et al.; Effects of ramped amplitude waveforms on the response of high-frequency mammalian nerve block; Journal of Neural Engineering; 4(4); pp. 390-398; Nov. 12, 2007.

Naples et al.; A spiral nerve cuff electrode for peripheral nerve stimulation; IEEE Transactions On Biomedical Engineering; 35(11); pp. 905-916; Nov. 1988.

Narang et al.; Functional capabilities of lower limb amputees; Prosthetics and Orthotics International; 8(1); pp. 43-51; Jan. 1, 1984.

NLLIC Staff. Fact Sheet. Amputation Statistics by Cause Limb Loss in the United States. Amputee Coalition of America (2008) 2 pages; retrieved from internet site http://www.amputee-coalitionsorg/fact_sheets/amp_stats_cause.pdf; Accessed Aug. 26, 2014; (year of pub sufficiently earlier than effective US filing date and any foreign priority date) 2008.

North et al.; Spinal cord stimulation versus re-operation in patients with failed back surgery syndrome: an international multicenter randomized controlled trial (Evidence study); Neuromodulation: Technology at the Neural Interface; 14(4); pp. 330-336; Jul. 2011.

Page et al.; Oral Posters—Intrathecal Drug Delivery for Pain and Spasticity: 2013 1630-1640; Spine; 11 June-004. Effect of intrathecal intermittent boluses and morphine concerntration on the incidence of inflammatory mass in a canine model; International Modulation Society; pp. 272-273; Jun. 11, 2013.

Pohjolainen et al.; Prosthetic use and functional and social outcome following major lower limb amputation; Prosthetics and Orthotics Intl.; 14(2); pp. 75-79; Jan. 1, 1990.

Polasek et al.; Stimulation stability and selectivity of chronically implanted multicontact nerve cuff electrodes in the human upper extremity; IEEE Transactions On Neural Systems And Rehabilitation Engineering; 17(5); pp. 428-437; Oct. 2009.

Saper et al.; Occipital nerve stimulation for the treatment of intractable chronic migraine headache: ONSTIM feasibility study; Cephalalgia; 31(3); pp. 271-285; Feb. 2011.

Schoppen et al.; Physical, mental, and social predictors of functional outcome in unilateral lower-limb amputees; Arch Phys Med Rehabil; 84(6); pp. 803-811; Jun. 1, 2003.

Sikka; Facial expression analysis for estimating pain in clinical settings; In Proceedings of the 16th International Conference on Multimodal Interaction; pp. 349-353; Nov. 2014.

Soin et al.; High-frequency electrical nerve block for post amputation pain: a pilot study; Neuromodulation; 16(5); 9 pages; Sep. 1, 2013.

Soin et al.; Feasibility study on high-frequency electrical nerve block for amputation pain; Neuromodulation; 14(6); p. 561; Nov. 1, 2011.

Subedi et al.; Phantom limb pain: mechanisms and treatment approaches; Pain Research and Treatment; Article ID 864605; 8 pages; (year of pub sufficiently earlier than effective US filing date and any foreign priority date) 2011.

Vaso et al.; Peripheral nervous system origin of phantom limb pain; Pain; 155(7); pp. 1384-1391; Jul. 1, 2014.

Waataja et al.; Effects of high-frequency alternating current on axonal conduction through the vagus nerve; J. Neural Eng.; 8(5); pp. 1-7; Sep. 15, 2011.

Ziegler-Graham et al.; Estimating the Prevalence of Limb Loss in the United States: 2005 to 2050; Arch Phys Med Rehabil; 89(3); pp. 422-429; Mar. 1, 2008.

Syed Shah et al.; U.S. Appl. No. 17/455,392 entitled "Apparatuses and methods for setting an electrical dose," filed Nov. 17, 2021.

* cited by examiner (not to scale)

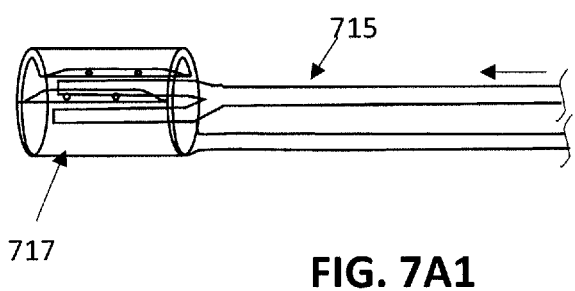
FIG. 7A1
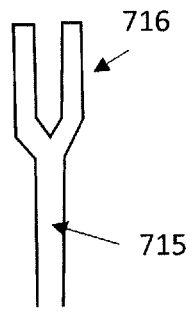
FIG. 7A2
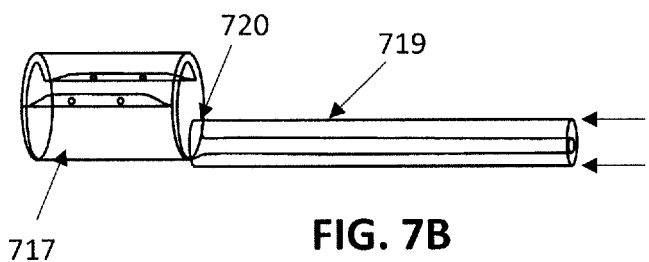
FIG. 7B
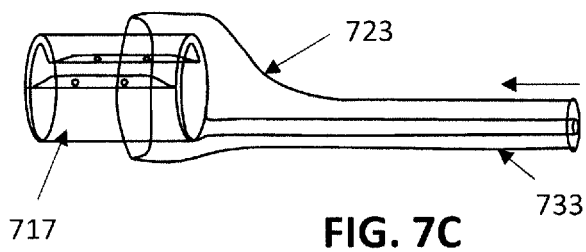
FIG. 7C
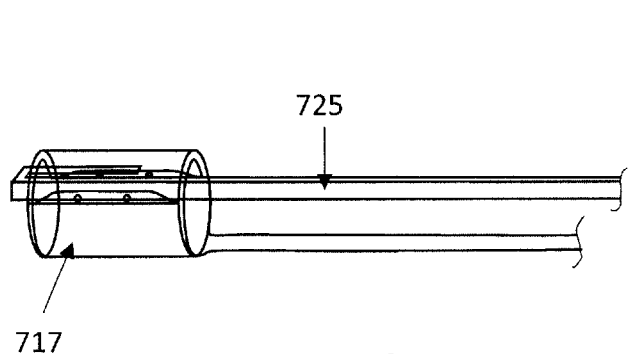
FIG. 7D1
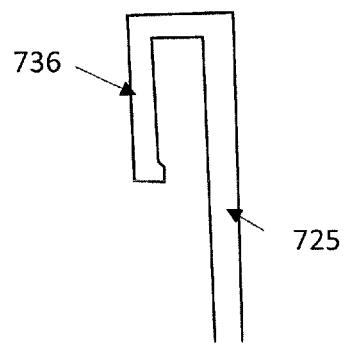
FIG. 7D2

NERVE CUFF DEPLOYMENT DEVICES

CROSS REFERENCE TO RELATED APPLICATIONS

This patent application is a continuation of U.S. patent application Ser. No. 16/954,049, filed on Jun. 15, 2020, titled "NERVE CUFF DEPLOYMENT DEVICES," now U.S. Publication No. US-2021-0008366-A1, which is a U.S. National Phase Application Under 35 U.S.C. § 371 of International Application No. PCT/US2018/065447, filed on Dec. 13, 2018, titled "NERVE CUFF DEPLOYMENT DEVICES," now PCT Publication No. WO 2019/118725, which claims priority to U.S. Provisional Patent Application No. 62/598,369, filed on Dec. 13, 2017, titled "NERVE CUFF DEPLOYMENT DEVICES," each of which is herein incorporated by reference in its entirety.

This patent may also be related to pending U.S. patent application Ser. No. 15/510,824, filed on Mar. 14, 2017, and herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The inventions described herein relate to the field of implantable neurostimulators.

BACKGROUND

Nerve cuffs (e.g., nerve cuff electrodes) may be used to apply energy to a nerve. For example, a nerve cuff electrode may have a plurality of segmented platinum contacts connected by at least one wire made of durable and biocompatible conductive material fashioned in a helical configuration. The nerve cuff electrode may include a plurality of conductive nerve contact segments, with the segments having an inner surface contacting a nerve trunk and an outer surface not contacting the nerve trunk; at least a single wire of a conductive biocompatible material operatively connecting the plurality of conductive nerve contact segments thus forming a segmented strip, the wire configured as helical portions separated by non-helical portions where the non-helical portions are secured to the surface of the conductive nerve contact segments not contacting the nerve trunk; and a conductive lead capable of operatively connecting a waveform generator to at least one of the plurality of nerve contact segments. FIGS. 1-3D illustrate an example of such a nerve cuff electrode.

For example, the nerve cuffs described herein may be applied to relatively large nerve, i.e., a nerve with a diameter exceeding about 3 mm and up to 12 mm. The nerve cuff may include a self-curling sheet of non-conductive material that includes a first layer, which is pre-tensioned, and a second layer, which is not pre-tensioned. The two layers are configured to form a cuff containing or holding strips of conductive material there between. The device may have one, two, three, four or more segmented strips of a conductive material that are disposed adjacent, but not transverse, to one longitudinally extending edge of the self-curling sheet, each of these strips of conductive material may be connected to an electrically conductive lead. The nerve cuff may contain one strip of a conductive material, termed a monopolar configuration, or at least two segmented strips, connected by an electrically conductive lead, of a conductive material, termed a bipolar configuration. The nerve cuff may contain three segmented strips, connected by an electrically conductive lead, of a conductive material, termed a tripolar configuration, or at least four segmented strips, connected by an electrically conductive lead, of a conductive material. Multiple apertures, typically circular but not necessarily so limited in shape, may be disposed at periodic intervals of the inner nerve-contacting surface along the curling length of one of the two non-conductive sheets or layers of the self-curling sheet/cuff. This may provide contact to the nerve by exposing and providing continuous multiple conductive contact points. The exposure may be at any interval that exposes as much of the conductive material as possible or desirable, and exceeds the contact surface area of conventional electrodes. Each of the first or top non-conductive sheet or layer and the second or bottom non-conductive sheet or layer may still retain and contain the conductive material therebetween, i.e., sandwiched inside the sheets or layers, so that the conductive material is in fact retained and does not pop out or come out while providing efficient current delivery. The non-conductive material may be silicone, the electrically conductive lead may be stainless steel, and the conductive material may be platinum. Other materials for each of the non-conductive material, the electrically conductive lead or wire, and the conductive material are known in the art. In use, the device may be operatively connected, e.g., by an external lead or wire, to a waveform generator that provides the regulated waveform.

The wire helical portions may be arranged along the wire length between the conductive nerve contact segments, and the wire non-helical portions may be secured to the conductive nerve contact segments by a plurality of spot welds. The wire helical portions may be embedded in a non-conductive material. The helical portions may be separated by non-helical portions that connect the conductive nerve contact segments. A second wire may operatively connect the plurality of nerve contact segments, with the second wire generally parallel with the first wire. The conductive nerve contact segments may be platinum, the wires may be stainless steel, and the non-conductive material may be silicone.

For example, FIG. 1 illustrates an implantable system including a nerve cuff 101, a lead 103 connecting the nerve cuff to a controller (e.g., waveform generator, control circuitry, power source, communications circuitry and/or antenna, etc.) 105. Systems including a nerve cuff such as those described herein, including those shown in FIGS. 1-3D, may be used to apply a high frequency nerve block to acutely treat pain, either acute pain or chronic pain (more than 6 months in duration), in humans by blocking nerve conduction on an action potential. Acute treatment may refer to on-demand treatment with substantially immediate pain relief effect. The nerve cuff may be applied onto a moderate and relatively large diameter nerves such as the sciatic nerve. One therapy involves reversibly blocking peripheral nerves by applying high frequency alternating current directly on a nerve trunk. Specifically, a current ranging from 5 kHz to 50 kHz may be applied; this may be referred to as a high frequency stimulation, compared to a current of less than 1 kHz applied in the conventional electrical stimulation described above. Efficacy of the high frequency alternating current therapy in acute non-human animal experiments (frog, cat) has been reported. U.S. Pat. Nos. 7,389,145 and 8,060,208 describe in general this electrical stimulation technology.

The nerve cuffs described herein may encircle a particular segment of a targeted peripheral nerve, e.g., a sciatic nerve, a tibial nerve. Using a patient-implanted electrode connected to an electrical waveform generator, an electrical waveform may be applied for a time interval, e.g., 10 min, sufficient to effect substantially immediate patient pain relief, e.g., within 10 min, and an extended period of pain relief up to several hours. The current may range, for example, from 4 mApp to 26 mApp. In general, electrical nerve block or activation in patients for pain management or other conditions may require a direct interfacing device with peripheral nerves in the form of a cuff wrapping around a nerve trunk. For example, U.S. Pat. No. 8,731,676 discloses a bipolar nerve cuff electrode with two continuous platinum strips embedded in a silicone substrate used to wrap around a nerve trunk. However, breakage of the platinum strips was found where a larger nerve trunk and/or certain anatomical characteristics (such as short stumps in above-knee amputees) were encountered. Inspections of explanted electrodes revealed that the platinum strips situated around the nerve trunk were wrinkled/creased or broken along their length due to repeated bending when the nerve trunk was compressed and flattened during daily activities. Platinum has a low mechanical strength despite its superior biocompatibility and electrical characteristics for charge delivery, thus, it may be beneficial to use multiple segmented platinum contacts, each segment connected with wires made of a durable and biocompatible conductive material, e.g., stainless steel (SS). The total surface area of all of the platinum contacts may be equivalent to that of a continuous strip by increasing the width to compensate for the gaps between the contacts. The configuration of the wire interconnection may establish the durability and flexibility of the cuff electrode. For example, a 7-strand of 316LVM wire may be wound into a helix. A gap may be created along the helix wherever it overlaps with a platinum contact. Conventional spot welding may be used for connecting the wire to the platinum contact. Two wire helices lying in parallel may be employed to provide redundancy. The helices may be entirely embedded in the silicone sheeting and only the outer side of the platinum contacts was exposed to the surface of the nerve trunk.

In use, the application of 10 kHz alternating current generated by a custom generator via a custom implanted nerve electrode may significantly reduce pain in the majority of patients treated. For example, an implantable electrode operatively connected to an external or implanted waveform generator may be used. The electrode may be a spiral cuff electrode similar to that described in U.S. Pat. No. 4,602,624. The electrode may be implanted in a human mammal on a desired peripheral nerve trunk proximal to the pain source (e.g., a neuroma), such that the cuff encircled the desired peripheral nerve in which the action potential was to be blocked. The cuff inner diameter may range from about 5 mm to about 12 mm. The sciatic nerve is known to have a relatively large nerve trunk; the diameter of the proximal part of the sciatic nerve in a human adult is about 12 mm. In one embodiment, the apparatus and method was used on the sciatic nerve to treat limb pain in above knee amputees. In one embodiment, the apparatus and method was used on the tibial nerve to treat limb pain in below knee amputees.

For example, FIG. 2A illustrates the use of a system including a cuff electrode applied to the sciatic nerve of an amputee patient. In this example, the amputee 107 has been implanted with a nerve cuff 101 around the sciatic nerve (nerve trunk), and is connected, via a lead 103, to the controller including the waveform generator 105. This procedure may be done, for example, by first dissecting to expose the nerve in an open procedure, then wrapping the nerve with the flexible (self-closing) cuff. Once implanted the controller/waveform generator may be placed in a pocket in the anterolateral abdominal wall, and a tunneling electrode cable may be positioned along the midaxilalary line (including transversely across the abdomen) to connect the controller/waveform generator to the nerve cuff electrode. Once the impedance of the nerve cuff is checked (e.g., by the controller) the incisions may be closed. The incision for implanting the nerve cuff is typically larger than about 1.5 inches (e.g., between 1.5 and 3 inches), so that sufficient visualization and access may be achieved.

Any reduction in the size of this access incision would be highly desirable. However, to date, because of the difficulty in accessing the nerve trunk of the amputee, only open procedures have been used. Described herein are methods and apparatuses (including systems and devices, which may specifically include access tools) for minimally invasively attaching a nerve cuff, and specifically nerve cuffs such as those described, e.g., in U.S. patent application no. US20170246453A1.

SUMMARY OF THE DISCLOSURE

Described herein is a deployment device to introduce a nerve cuff electrode via minimal surgical incision, including a cannula accommodating, e.g., a 13 mm diameter. The nerve cuff electrode may be deployed via an apparatus such as an introducer tool which encapsulates the electrode (e.g., in some variations via a two-part compartment) and provides support for visualizing and positioning the nerve cuff, protecting the nerve cuff electrode, so that it can be implanted in the desired location in a minimally invasive manner.

In some variations, the introducer capsule is delivered and pushed through the cannula (e.g., trocar), once the nerve target is identified and exposed via the cannula. In any of these variations, endoscopic visualization may be used as part of the deployment; the delivery tool may couple with or integrate with an endoscope, or may be used separately from the endoscope. In some variations, the delivery tool may then be detached; for example, in variations including a two-part capsule, the capsule may be detached, and the electrode remains may be implanted near the target nerve site; the delivery tool (e.g., capsule) may then be removed from the cannula. The electrode may be unrolled via forceps, placed around the targeted nerve and sutured closed via two suture loops.

For example, described herein are methods of minimally-invasively attaching a nerve cuff electrode to a patient's nerve (e.g., nerve root). Any of these methods may include: minimally invasively inserting a cannula (which may be part of a trocar) into the patient's body (e.g., tissue) to a nerve root region; inserting a nerve cuff deployment tool into the cannula, wherein the nerve cuff electrode is attached at a distal end of an elongated body of the nerve cuff deployment tool, further wherein the elongated body of the nerve cuff deployment tool has a column strength sufficient to resist buckling at compressive forces of at least a predetermined amount (e.g., 2 N, 5 N, 10 N, 15 N, 20 N, 25 N, 30 N, etc.); advancing the nerve cuff deployment tool distally through the cannula into the nerve root region; and disengaging the nerve cuff from the nerve cuff deployment tool and coupling the nerve cuff to the patient's nerve root.

Any of these methods may also include visualizing the nerve root region. For example any of these methods may include inserting a visualization tool into the nerve root region and visualizing the nerve root region. The visualization tool (e.g., a scope) may be separate from the cannula, or it may be combined with/coupled to the cannula. For example, the visualization tool may include a cannula and may visualize the distal end of the cannula, e.g., near the nerve root region. The scope may include illumination. The scope may include a camera.

The cannula may be inserted as part of a trocar. For example, a trocar having a cutting portion (e.g., an obturator) and a cannula may also include a seal and may be minimally invasively inserted into the body as part of any of these methods. For example, minimally invasively inserting the cannula may include inserting a trocar through the patient's tissue to the nerve region, wherein the cannula forms a part of the trocar.

In general, the nerve root region includes a region around the nerve root onto which the nerve cuff electrode is to be positioned. The nerve root region may be proximal to neuroma (e.g., in an amputated region) and may include the nerve root and any surrounding tissues; alternatively or additionally the surrounding tissues may be removed (e.g., through the cannula) or retracted to create a clearing for insertion of the nerve cuff electrode.

Any of these methods may include removably attaching the nerve cuff electrode to the distal end of the elongated body of the nerve cuff deployment tool. For example, the nerve cuff electrode may be held within a chamber (e.g., capsule) of the nerve cuff deployment tool. Alternatively or additionally, the nerve cuff deployment tool may be connected by a clip, clamp, etc. to the nerve cuff electrode. The nerve cuff deployment tool may be configured to attach to a predetermined portion of the nerve cuff electrode; alternatively, the nerve cuff deployment tool may be configured to connected and hold to any region of the nerve cuff electrode. In some variations the nerve cuff deployment tool includes a nerve cuff engagement region that is configured to removably attach to the nerve cuff electrode. Examples of nerve cuff attachment or engagement regions are described below.

Any of the methods of operation described herein may include removably attaching the nerve cuff to the distal end of the nerve cuff deployment tool. This may include least partially enclosing the nerve cuff within a chamber of the nerve cuff deployment tool (e.g., within a sleeve, opening, cup, chamber, etc. of the nerve cuff deployment tool distal end, forming part of the nerve cuff engagement region. Alternatively, removably attaching the nerve cuff may comprise fully enclosing the nerve cuff, e.g., within a capsule region at a distal end of the nerve cuff deployment tool.

Inserting the nerve cuff deployment tool may include inserting the nerve cuff deployment tool with the nerve cuff attached wherein the nerve cuff is a self-rolling nerve cuff electrode. Self-rolling nerve cuffs as described, for example, in U.S. patent application Ser. No. 15/510,824, filed on Mar. 14, 2017, herein incorporated by reference in its entirety. The nerve cuff electrode may be held in a constrained (e.g., collapsed, constricted, etc.) configuration by the nerve cuff deployment tool.

The elongated body of the nerve cuff deployment tool may be flexible or rigid. In some variations, the nerve cuff deployment tool has a flexible elongated body (which still maintains sufficient column strength as indicated above), so as to navigate a bent or curved cannula for delivery.

Advancing the nerve cuff deployment tool distally through the cannula into the nerve root region may include positioning a distal end of the nerve cuff deployment tool adjacent to the nerve root within the nerve root region. For example, the distal end of the cannula may be positioned immediately adjacent to the nerve (e.g., within about 1 mm) or closely adjacent (e.g., within about 10 mm).

Disengaging the nerve cuff electrode from the nerve cuff deployment tool may include activating a detachment mechanism at the proximal end of the nerve cuff deployment tool. In some variations the nerve cuff electrode is disengaged by separating or opening two parts (e.g., halves) of a capsule to release the nerve cuff electrode; this may be done by proximally manipulating the nerve cuff deployment tool to separate the two portions forming the capsule, releasing the nerve cuff electrode and removing the portion of the nerve cuff deployment tool forming the capsule back into the catheter. For example, disengaging the nerve cuff from the nerve cuff deployment tool may include separating two halves of a nerve cuff capsule at the distal end of the nerve cuff deployment tool. In some variations a separate pusher is included having a distal end configured to apply distal force to the nerve cuff electrode. Thus, any of these methods may include pushing or holding the nerve cuff electrode using the pusher to separate or disengage the nerve cuff electrode from the rest of the nerve cuff deployment tool.

Either before, during or after disengaging the nerve cuff electrode from the nerve cuff deployment tool, the nerve cuff may be wrapped (e.g., rolled) around the nerve. For example, in some variations, the nerve cuff electrode may be wrapped around the nerve root when released from the nerve cuff deployment tool. The nerve cuff electrode may be held in an inverted configuration within the nerve cuff deployment tool, so that, when released from the nerve cuff deployment tool, it is biased to wrap itself around the nerve root; thus, the nerve cuff deployment tool may position the nerve cuff sufficiently near or adjacent to the nerve root so that it may automatically wrap itself around the nerve root. Alternatively or additionally, the nerve cuff electrode may be manipulated by, e.g., a laparoscopic or other tool (e.g., forceps, etc.) to position or wrap around the nerve root. For example, any of these methods may include extending one or more manipulators (e.g., pairs of manipulators) through the cannula to wrap the nerve cuff around the nerve root.

For example, a method of minimally-invasively attaching a nerve cuff electrode to a patient's nerve root may include: minimally invasively inserting a cannula the patient's tissue to a nerve root region; inserting a nerve cuff deployment tool into the cannula, wherein the nerve cuff electrode comprises a self-curling nerve cuff electrode that is removably attached at a distal end of an elongated body of the nerve cuff deployment tool, further wherein the elongated body of the nerve cuff deployment tool has a column strength sufficient to resist buckling at compressive forces of at least 10 N; advancing the nerve cuff deployment tool distally through the cannula into the nerve root region; and disengaging the nerve cuff from the nerve cuff deployment tool and wrapping the nerve cuff to the patient's nerve root.

In general, a nerve cuff deployment apparatus for minimally invasively attaching a nerve cuff electrode to a patient's nerve root may include: an elongated body having a column strength sufficient to resist buckling at compressive forces of at least some predetermined amount of force (e.g., 2 N, 3 N, 4 N, 5 N, 6 N, 7 N, 8 N, 9 N, 10 N, 12 N, 15 N, 20 N, 25 N, 30 N, etc.); and a nerve cuff engagement region at a distal end of elongated body, configured to releasably secure to a nerve cuff electrode.

Any of these systems may include the nerve cuff electrode as part of the system, which may be pre-loaded. For example, any of these systems may include a self-curling nerve cuff electrode, as described herein. Thus, the system may include a self-curling nerve cuff releasably coupled to the nerve cuff engagement region.

The elongated body may be flexible. In some variation, the elongated body is rigid.

In some variations the apparatus is configured to form an enclosure to hold the nerve cuff electrode. For example, the elongated body may include a first half and a second half, wherein the nerve cuff engagement region comprises a first capsule portion at the distal end of the first half and a second capsule portion at the distal end of the second half, wherein the first and second capsule portions are configured to couple to form a capsule to enclose and protect the nerve cuff electrode.

In some variation, the nerve cuff engagement region includes a flared-open distal-facing region chamber configured to at least partially enclose the nerve cuff electrode. Alternatively or additionally, the nerve cuff engagement region may include a hook or fork configured to releasably engage with the nerve cuff electrode. The nerve cuff engagement region may hold the expandable (curling) wings of the nerve cuff electrode or to the base of the nerve cuff electrode, e.g., where the wire(s) extending from the nerve cuff electrode extend proximally. In some variations, the nerve cuff engagement region comprises a rounded distal end configured to engage with the nerve cuff electrode. The rounded distal end may be configured to support against the nerve cuff electrode without damaging the nerve cuff electrode, e.g., by pushing against it. In some variations nerve cuff engagement region includes a passage for holding the lead extending from the nerve cuff.

As mentioned, any of these apparatuses may include a pusher (e.g., a nerve cuff pusher) extending adjacent to the elongated body and having a distal end configured to apply distal force to the nerve cuff electrode. The pusher may extend within the elongated body of the nerve cuff deployment apparatus. The distal-facing end of the pusher (the distal end) may be configured to engage with the nerve cuff electrode. For example, the distal-facing end of the pusher may include a forked distal end that is configured to engage with the nerve cuff electrode.

In any of these variations, the nerve cuff deployment apparatus may include a proximal control coupled to the elongated body configured to disengage the nerve cuff engagement region from the nerve cuff electrode. The proximal control may include a handle, grip, button, switch, slider, or the like. For example, the proximal control may be a handle coupled to a slider that allows the apparatus to engage with the pusher, for example, and/or the halves of the elongated body that can be (in some variations) separated to release the nerve cuff electrode.

For example, a nerve cuff deployment apparatus for minimally invasively attaching a nerve cuff electrode to a patient's nerve root may include: an elongated body having a column strength sufficient to resist buckling at compressive forces of at least 10 N, wherein the elongated body comprises a first half and a second half, each extending distally to proximally; and a nerve cuff engagement region at a distal end of elongated body, configured to releasably secure to a nerve cuff electrode, wherein the nerve cuff engagement region further comprises a first capsule portion at the distal end of the first half and a second capsule portion at the distal end of the second half, wherein the first and second capsule portions are configured to form a capsule to enclose and protect the nerve cuff electrode.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

In FIG. 4A, access to the nerve trunk onto which the nerve cuff is to be applied is achieved using a trocar or cannula; a visualization tool (e.g., an endoscope for endoscopic visualization) is also shown allowing the physician to view the application directly. In FIG. 4B, a nerve cuff deployment device (tool) is used to support and protect the nerve cuff (e.g., self-rolling nerve cuff) so that it may be minimally invasively delivered to the nerve root and deployed for attachment over the nerve root.

FIG. 6A shows the tool assembled to form a capsule that surrounds and protects the nerve cuff electrode. FIG. 6B shows an exploded view of the nerve cuff deployment tool of FIG. 6A, which may be assembled to fully enclose the nerve cuff electrode.

In FIG. 6C the nerve cuff deployment tool forms a capsule at the distal end to fully enclose the nerve cuff electrode; a pusher extends adjacent to and within the elongated body to apply distal force to the nerve cuff electrode. FIG. 6D shows an exploded view of the nerve cuff deployment tool of FIG. 6C.

FIGS. 7A1-7A2 show another example of a nerve cuff deployment tool that includes a flexible deployment tool having high column strength that may be releasably attached to the self-curling nerve cuff (as shown in FIG. 7A1) and used to push or pull the nerve cuff within a delivery cannula or trocar. FIG. 7A2 shows the tool unconnected to a nerve cuff.

FIG. 7B shows another example of a flexible deployment tool having a high column strength that may be used to push (or in some variations, pull) the self-curling nerve cuff distally through a delivery cannula or trocar for minimally invasive insertion, as described herein.

FIG. 7C shows another example of a flexible deployment tool having a high column strength that may be used to push (or in some variations, pull) the self-curling nerve cuff distally through a delivery cannula or trocar for minimally invasive insertion, as described herein.

FIGS. 7D1 and 7D2 show another example of a nerve cuff deployment tool that includes a flexible deployment tool having high column strength that may be releasably attached to the self-curling nerve cuff (as shown in FIG. 7) and used to push or pull the nerve cuff within a delivery cannula or trocar.

In FIG. 8A, the nerve cuff is hinged (e.g., two-part) nerve cuff. FIG. 8B shows the hinged nerve cuff of FIG. 8A wrapped around a nerve in an end view and FIG. 8C shows the hinged nerve cuff of FIG. 8A in an external perspective view on the nerve trunk.

DETAILED DESCRIPTION

In general, described herein are methods and apparatuses, including in particular tools such as nerve cuff deployment tools and methods of using them, for minimally invasively attaching a nerve cuff to a nerve trunk. In particular, described herein are methods and apparatuses for delivering nerve cuff electrode (particularly self-rolling nerve cuff electrodes) through an elongated cannula or other elongated, minimally invasive channel for deployment at, near or on a nerve root. In general, a nerve cuff deployment apparatus for minimally invasively attaching a nerve cuff electrode to a patient's nerve root may have a sufficient column strength (e.g., a column strength sufficient to resist buckling at compressive forces of at least 2 N, 5 N, 7 N, 8 N, 9 N, 10 N, 15 N, etc.) so that it may support and protect the generally flexible and loose nerve cuff electrode prior to placing it on the nerve root. The nerve cuff deployment device generally includes a nerve cuff engagement region at a distal end of elongated body that is configured to releasably secure to a nerve cuff electrode to be delivered.

As already discussed above, FIGS. 1-2A illustrate current methods for positioning or placing a nerve cuff onto a nerve root. For example, in an above-the-knee amputee, a nerve cuff may be placed approximately 5 cm proximal to the neuroma on the sciatic nerve; prior to the inventions described herein, this required a long incision (e.g., 8-10 cm in length), e.g., between the biceps femoris and semimembranosus/semitendinosus region of the body. The nerve cuff (e.g., such as shown in FIGS. 2B and 3A-3D) would then be positioned over and around the exposed nerve root. FIG. 3A-3D illustrates one example of this technique. For example, by exposing the nerve, e.g., by dissecting away material around the nerve, including in some cases cauterizing the tissue around the nerve, the nerve cuff electrode 303 may be pulled, e.g., by use of forceps 305 under and around the nerve. The cuff may be initially bathed in an antibiotic solution. Forceps (e.g., right angle forceps) may be used to gently pull the cuff underneath the nerve (FIG. 3B), and the cuff may be wrapped around the nerve, as shown in FIGS. 3C-3D. The electrode cable runs superiorly away from the cuff (e.g., distally).

Figure 2A:
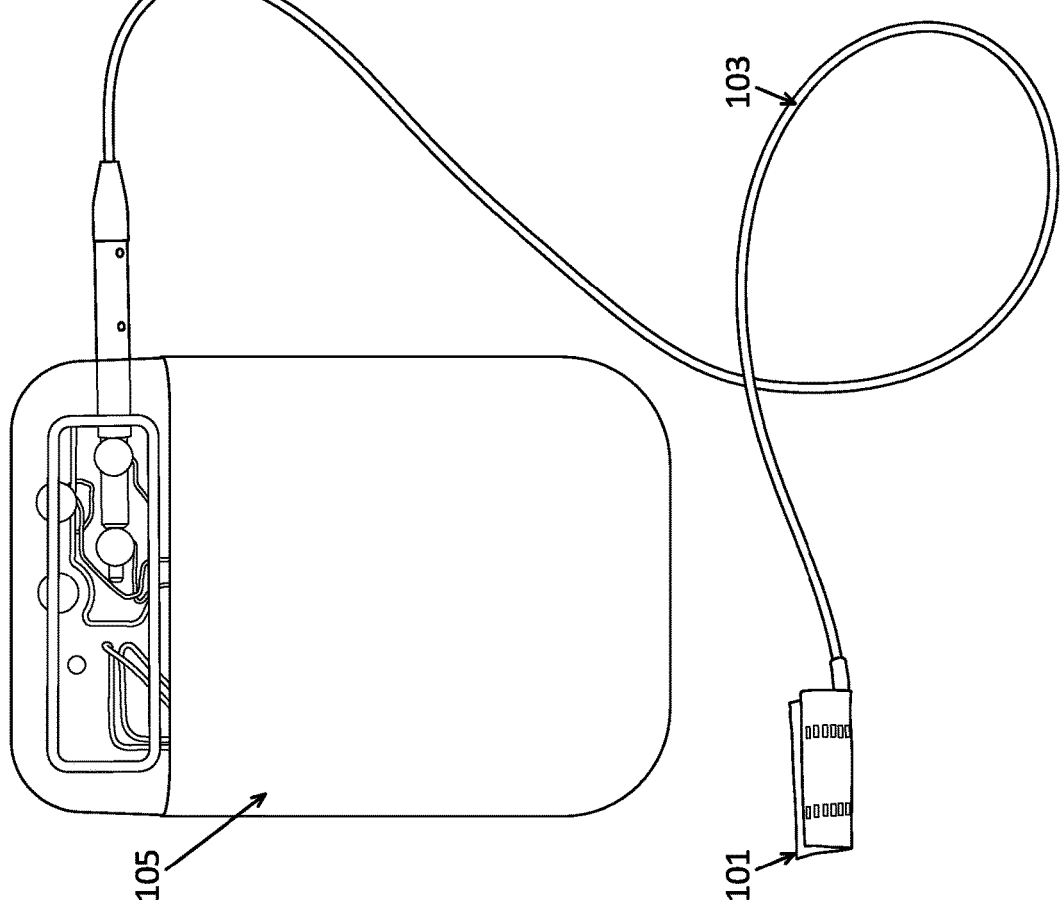
FIG. 2A shows an example of the system of FIG. 1 implanted into a patient.
Figure 2B:
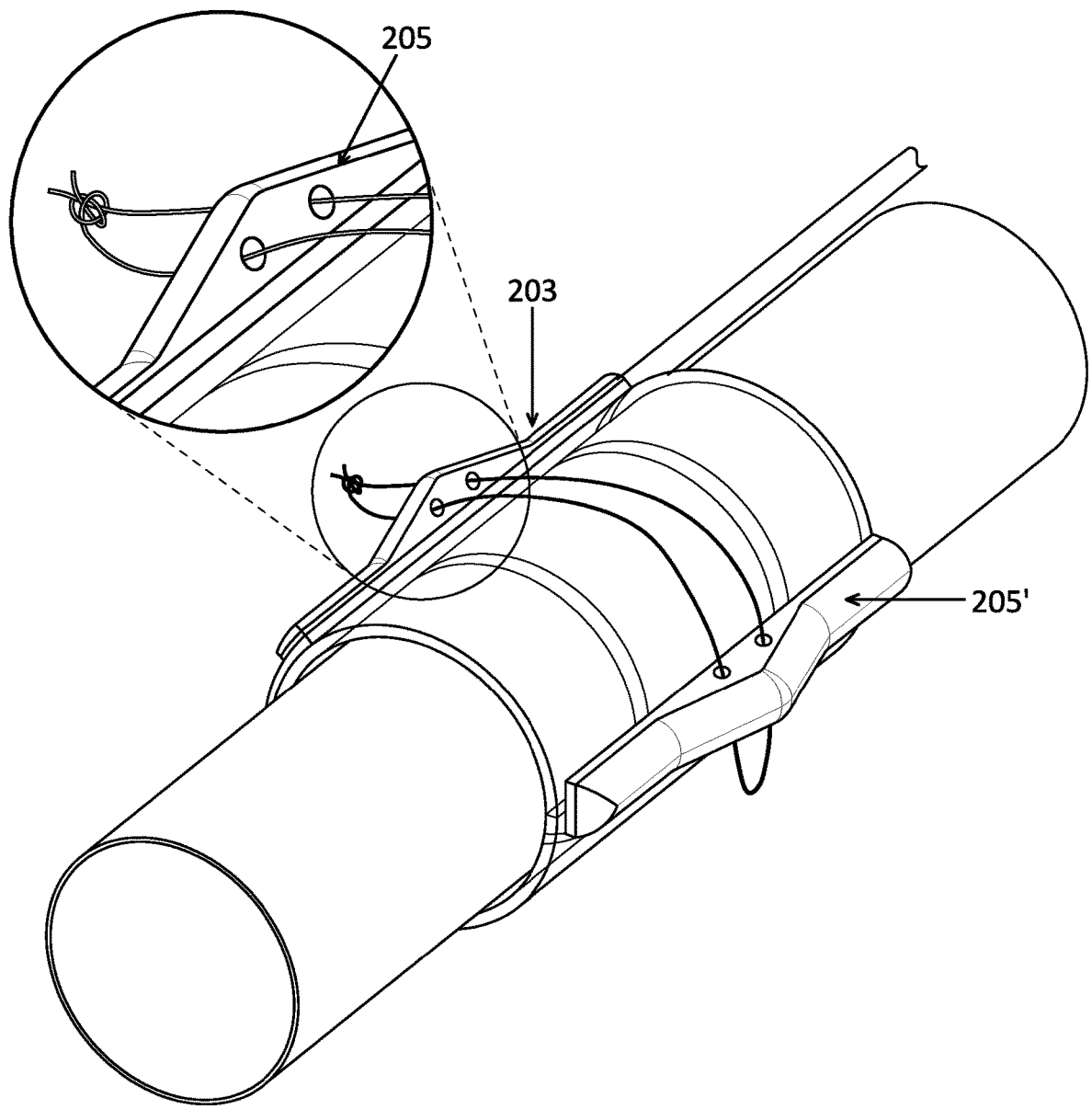
FIG. 2B schematically illustrates the attachment of and nerve cuff such as the one shown in FIGS. 1-2A onto a nerve trunk.
Figure 3A:
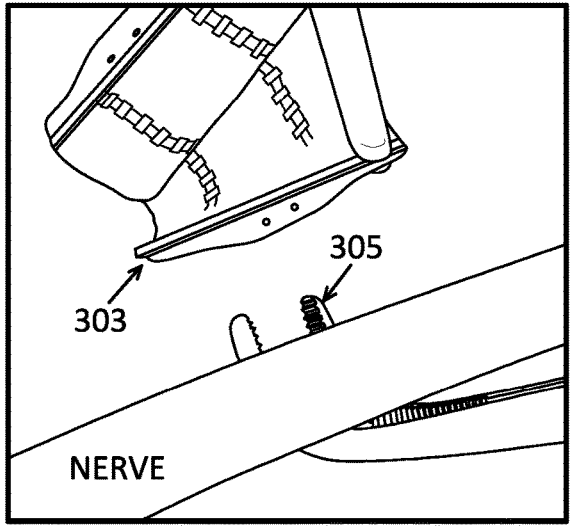
FIGS. 3A-3D illustrate application of a self-curling nerve cuff onto a model of a nerve trunk.
Figure 3B:
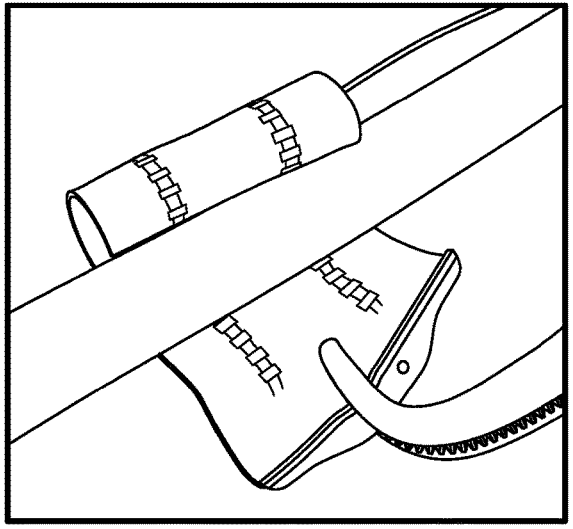
Figure 3C:
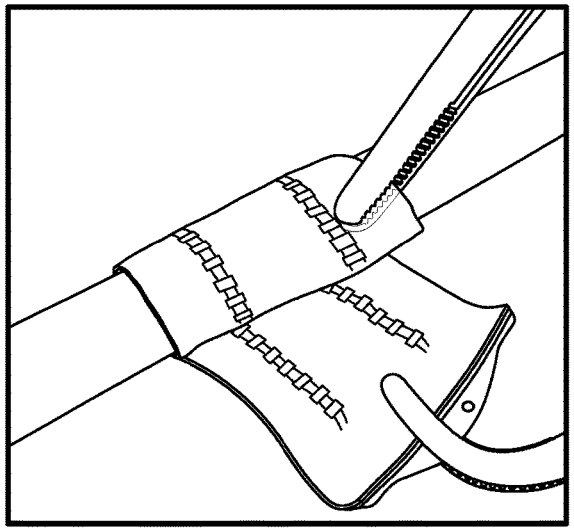
Figure 3D:
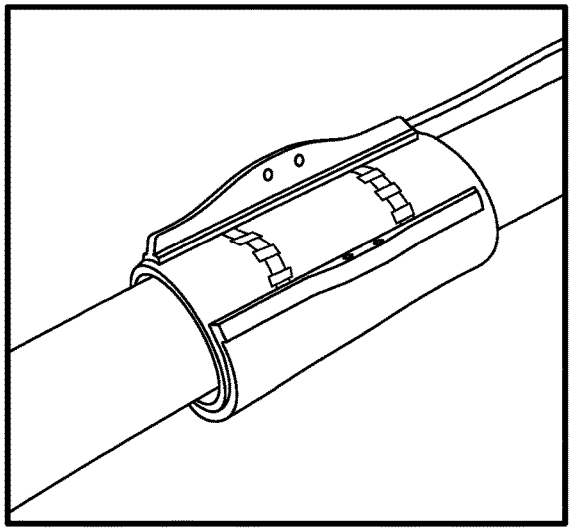

Although any appropriate nerve cuff may be used, in particular, the nerve cuff may be a self-wrapping nerve cuff, such as illustrated in FIG. 2B. In this example, the nerve cuff 203 includes two proud regions 205 that each include suture holes through which a suture to secure the two regions together around the nerve may be positioned. The proud region extend up (e.g., 90 degrees) from the curved/curling plane of the arms forming the nerve cuff electrode. The first proud region is separated from the second proud region by less than the expected circumference of the nerve root onto which the nerve cuff is to be applied (e.g., +/−50% of the average expected circumference, or within 50% of the expected circumference), on one side of the wings, so that one "wing" may wrap against the nerve root and the other wing (with the two proud regions) may extend from the other wing and wrap over the first wing, as shown.

Figure 4A:
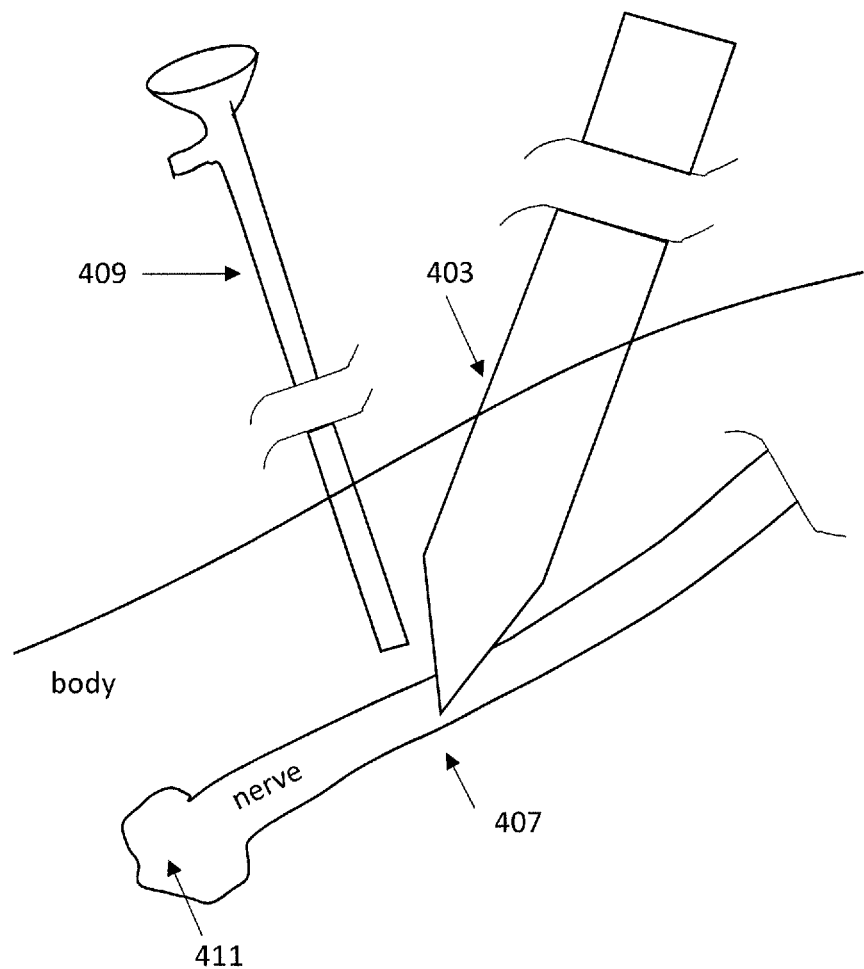
FIGS. 4A-4B illustrate one example of a method for minimally-invasively applying a self-rolling nerve cuff onto a nerve trunk as described herein.
Figure 4B:
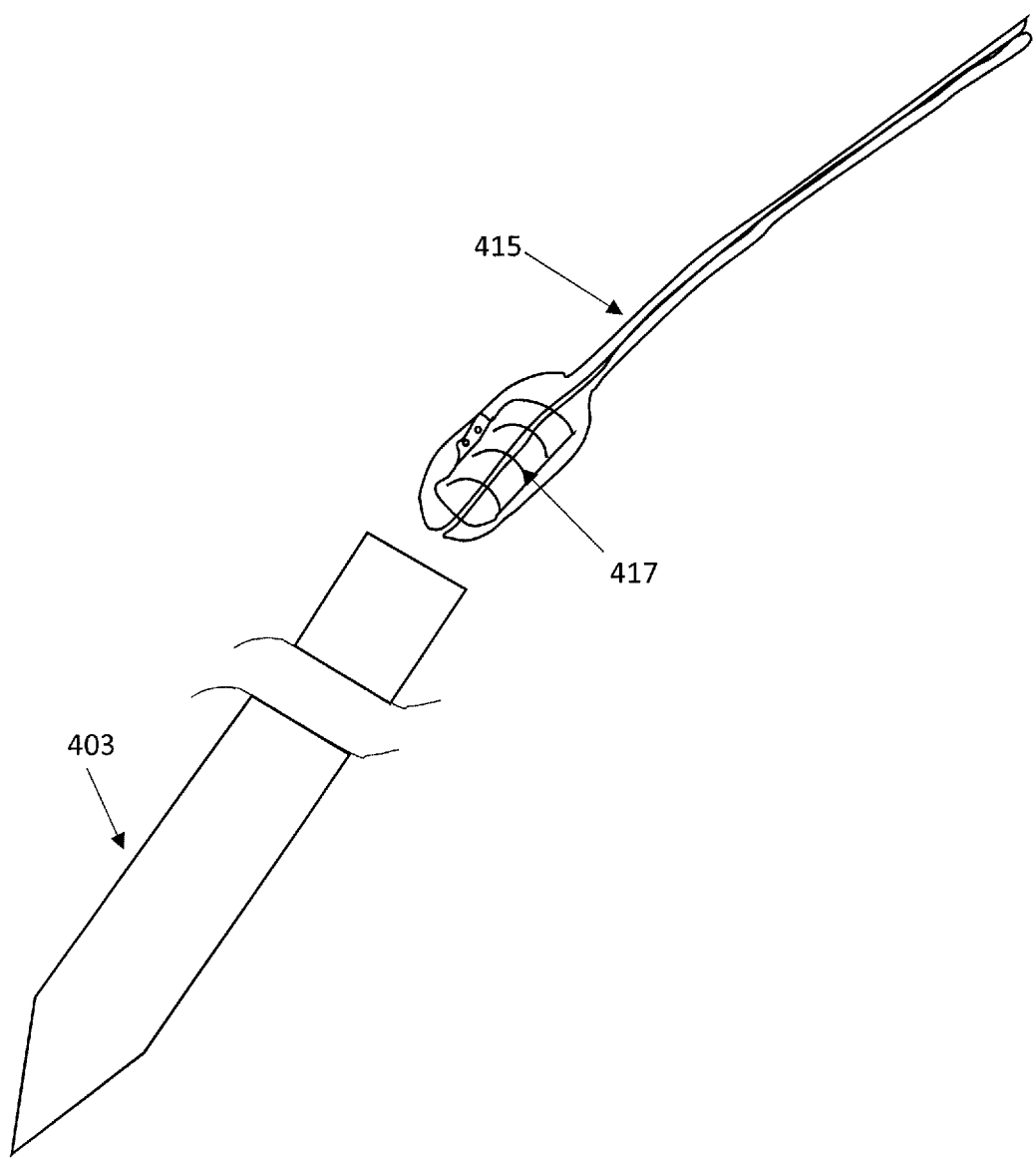

Described herein are methods of less invasively applying a nerve cuff electrode onto a nerve root, including methods of minimally invasively applying the nerve cuff electrode that do not require a large incision. For example, FIGS. 4A-4B illustrate a general method of less invasively applying a nerve cuff, including the use of a nerve cuff deployment tool as described herein. In FIG. 4A, a trocar 403 including a cannula) is first inserted into the body to the region of the nerve root region 407 onto which the nerve cuff electrode is to be positioned. In this example, the nerve root region is just proximal to a neuroma 411. Prior to inserting the trocar/cannula, a visualization tool such as an endoscope 409 may be inserted into the body to visualize the nerve root region. In this example, the endoscope is a rigid endoscope; any appropriate endoscope may be used. Once the trocar is used to position the cannula with a distal end opening into the nerve root region, the nerve cuff electrode may be inserted through the cannula and onto the nerve root. In general the nerve cuff electrode is loose, and overly flexible, so that it cannot be easily inserted through a cannula. Instead, as shown in FIG. 4B, a nerve cuff deployment device 415 may be used to deliver the nerve cuff electrode through the cannula and into position.

In FIG. 4B, the nerve cuff deployment device 415 includes a two-part elongated body that ends in a pair of halves that form a capsule 413 which may hold a nerve cuff electrode 417, a shown. In this example, the nerve cuff deployment device therefore include an elongated region that can be pushed to drive the capsule and therefore the nerve cuff electrode distally through the cannula.

Figure 5A:
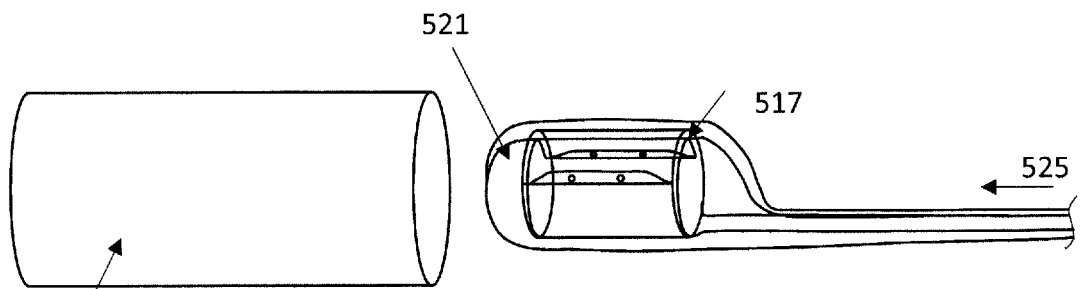
FIGS. 5A-5G illustrate a method of minimally invasively applying a self-rolling nerve cuff onto a nerve trunk using one variation of a nerve trunk deployment tool, in greater detail.
Figure 5B:
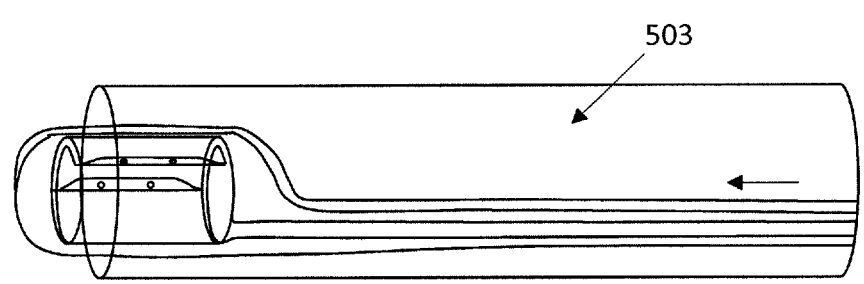
Figure 5C:
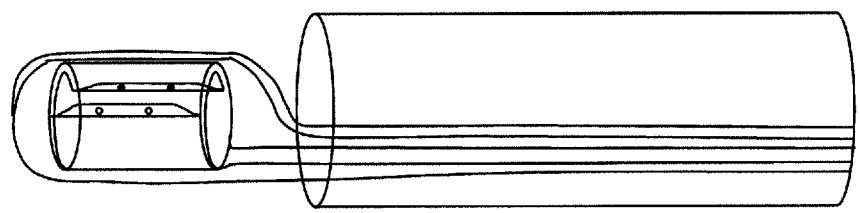
Figure 5D:
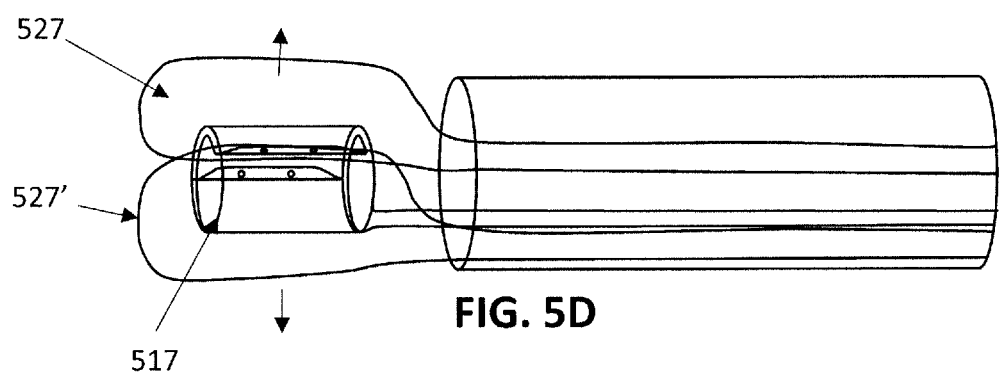
Figure 5E:
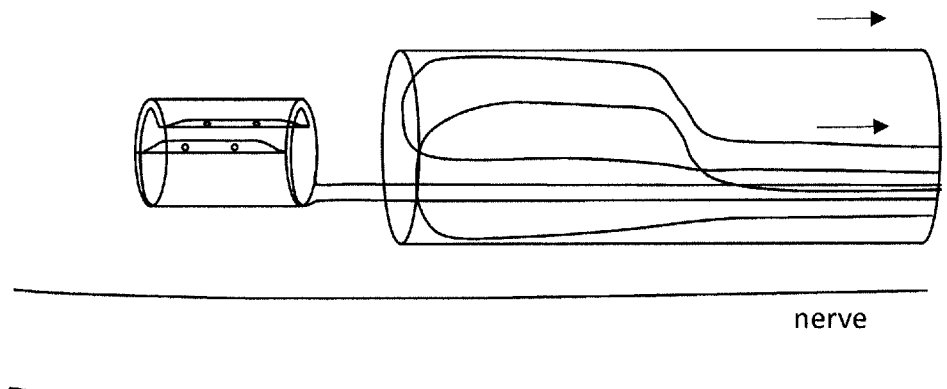
Figure 5F:
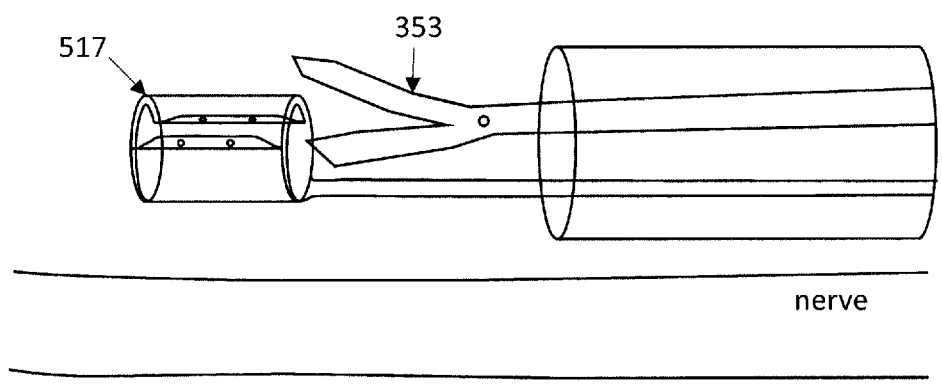
Figure 5G:
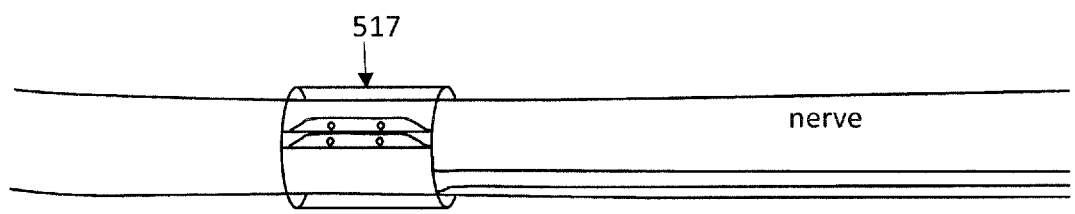

FIGS. 5A-5G illustrate this method in additional detail. For example, in FIG. 5A, the nerve cuff electrode 517 is held within a nerve cuff engagement region forming a capsule 521; the lead coupled to the nerve cuff electrode is either also held within the capsule or extends proximally through the nerve cuff deployment device. In FIG. 5A, the nerve cuff deployment device is already loaded with the nerve cuff electrode; once the catheter 503 is positioned, the nerve cuff deployment device may be driven distally (e.g., by pushing on the proximal end 525) and extended out of the distal end of the catheter, as shown in FIGS. 5B-5C. Thereafter, the nerve cuff electrode may be disengaged from the nerve cuff deployment tool by separating the two halves 527, 527' of the nerve cuff capsule; this may be done at the distal end of the nerve cuff deployment tool, as shown in FIG. 5D. These separated halves may then be withdrawn back into the catheter and/or fully removed, as shown in FIG. 5E. In some variations, an additional step of using a tool such as an endoscope manipulator 535 may be used to help wrap the nerve cuff electrode around the nerve root ("nerve") as shown in FIG. 5G. In some variations the nerve cuff electrode may be held inverted within the capsule, so that the arms of the nerve cuff electrode are wrapped in the opposite direction. In this case, a self-wrapping nerve cuff may be biased to automatically wrap around the nerve root, or wrap around with assistance, e.g., from a minimally invasive manipulator.

Figure 6A:
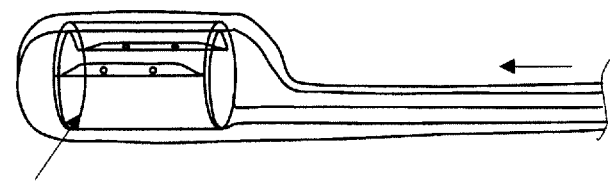
FIGS. 6A and 6B illustrate the nerve cuff deployment tool shown in FIGS. 5A-5E.
Figure 6B:
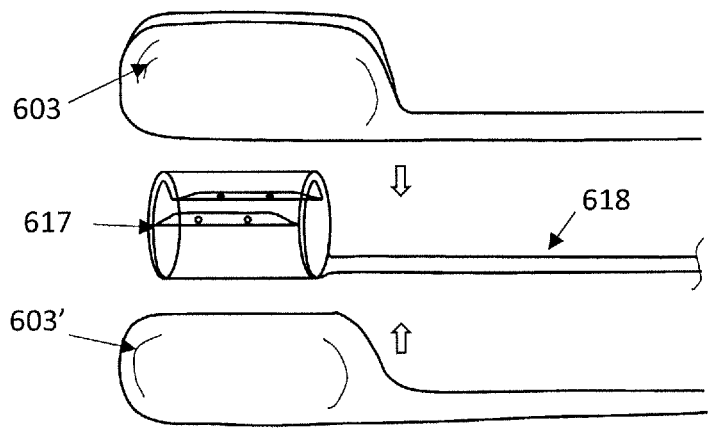

FIGS. 6A and 6B illustrate the nerve cuff deployment tool variations shown in FIGS. 5A-5G, which includes a capsule region that encloses and protects (and may constrain) a nerve cuff electrode. In FIG. 6A the nerve cuff deployment tool is pre-loaded to include the nerve cuff electrode. FIG.

Figure 6C:
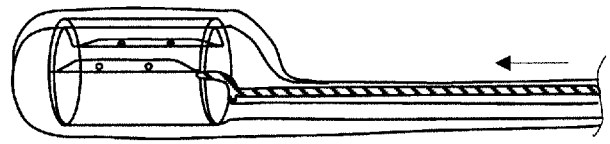
FIGS. 6C and 6D illustrate a nerve cuff deployment tool similar to that shown in FIG. 6A-6B.
Figure 6D:
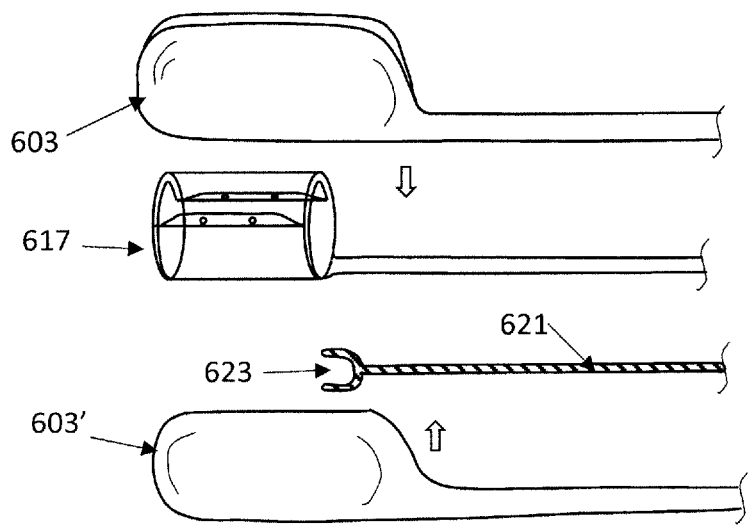

6B shows an exploded view in which a left half 603 and a right half 603' of the nerve cuff engagement region forming the enclosed capsule is shown. In FIG. 6B, the two halves may be closed over the nerve cuff electrode and either coupled together or held together within the cannula. The nerve cuff electrode 617 includes a highly flexible lead 618 that may also be held within the capsule, or it may be within the elongated body of the nerve cuff deployment tool. FIGS. 6C and 6D illustrate a similar variation of the nerve cuff deployment tool that also includes an inner pusher 621. The pusher may be coupled to the nerve cuff electrode (in FIG. 6C-6D, the pusher is shown to include a forked distal end 623 to engage with the rolled nerve cuff electrode within the capsule. In this example, the pusher is a high-column strength member than can either hold the nerve cuff electrode in position when disengaging from the nerve cuff deployment tool or may drive the nerve cuff electrode distally (e.g., towards the nerve root) when deploying.

FIGS. 7A1-7D2 illustrate other variations of nerve cuff deployment tools that may be used with any of the methods descried herein. Elements from any of the nerve cuff deployment tools shown in any of the variations and embodiments described may be used with any of other variation or embodiment of a nerve cuff deployment tool. For example, a pusher such as the one shown in FIG. 6C-6D may be used with any of the nerve cuff deployment tools shown in FIG. 7A1-7D2.

Figure 1:
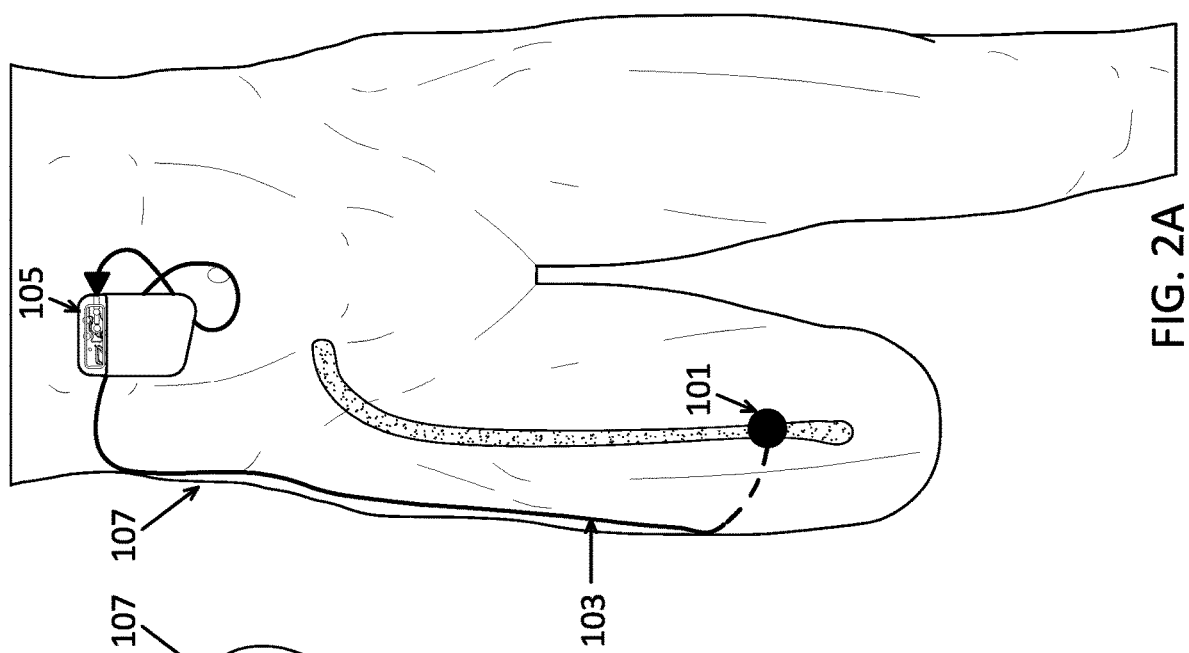
FIG. 1 shows one example of a nerve cuff system (including nerve cuff, lead and implantable controller/waveform generator).

FIG. 7A1 shows a nerve cuff deployment tool 715 releasably coupled to a nerve cuff electrode 717. In this example, the nerve cuff deployment tool has a bifurcated end 716 (e.g., forked or split) that may couple and engage with the nerve cuff electrode, and particularly the wrapping arms of the nerve cuff electrode. In some variations one or both arms may be hinged so as to close (e.g., clamp) onto each other to releasably secure the nerve cuff assembly between them; a control (e.g., handle, etc. on the distal end of the nerve cuff deployment tool may be operated to release the arms of the nerve cuff deployment tool. FIG. 7A2 shows a perspective view of the nerve cuff deployment tool not coupled to the nerve cuff.

FIG. 7B shows another variation of a nerve cuff deployment tool 719 having a distal end that is rounded 720 to apply force to a portion of the nerve cuff electrode 717 without damaging it. In this example the nerve cuff deployment tool is a hollow member that receives the lead connected to the nerve cuff assembly and provide structural support to drive the nerve cuff electrode distally. The lead may be held within the nerve cuff deployment tool in tension, so that the nerve cuff assembly is secured to the distal end of the nerve cuff deployment tool.

FIG. 7C shows another example of a nerve cuff deployment tool 723 that includes a partial capsule that is distally open. The distal-facing end region may hold (and constrain expansion of) the nerve cuff electrode 717 until it is deployed; for example by withdrawing the nerve cuff deployment tool elongated body 733 proximally while holding a pusher (not shown) in place relative to the patient's body, or advancing it slightly distally.

FIGS. 7D1 and 7D2 show another example of a nerve cuff deployment tool 725 in which the nerve cuff engagement region 736 at the distal end of the nerve cuff deployment tool is configured to releasably couple with the nerve cuff electrode 717. This variation is similar to that shown in FIGS. 7A1-7A2, but may extend over the distal side of the nerve cuff electrode, allowing it to be both pulled and pushed robustly. This variations may also include a release, e.g., at the proximal end, and the distal end region may be hinged in one or more positions to remove the connection to the nerve cuff electrode. Alternatively, in some variations a pusher such as that shown in FIG. 6C-6D may be used to disengage the nerve cuff electrode from the nerve cuff deployment tool.

Figure 8A:
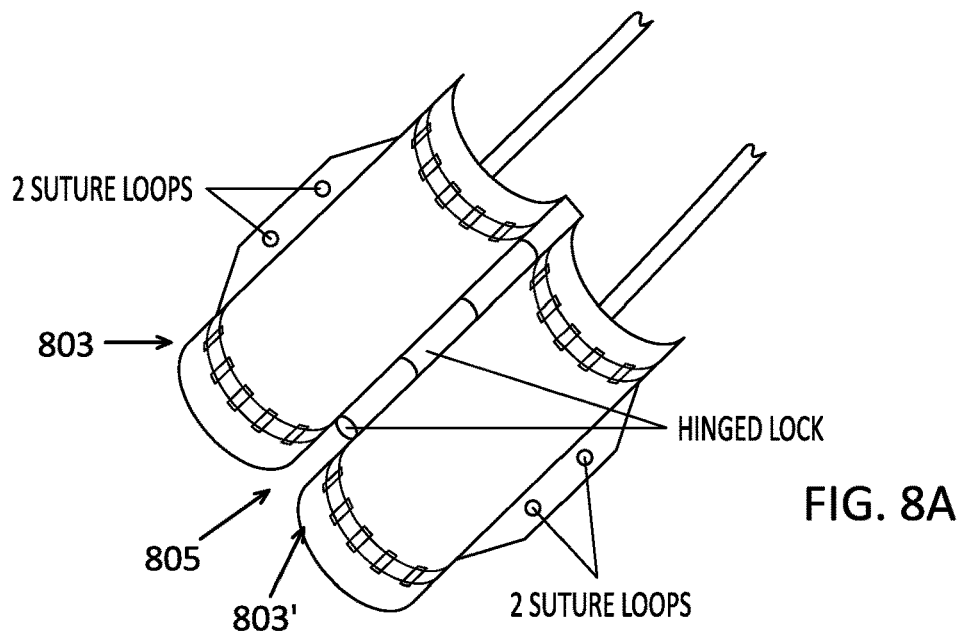
FIGS. 8A-8C illustrate alternative examples of nerve cuffs that may be used with any of the methods and apparatuses described herein.
Figure 8B:
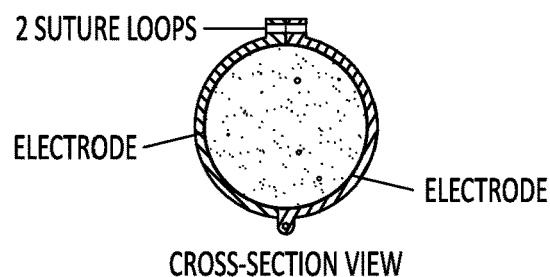
Figure 8C:
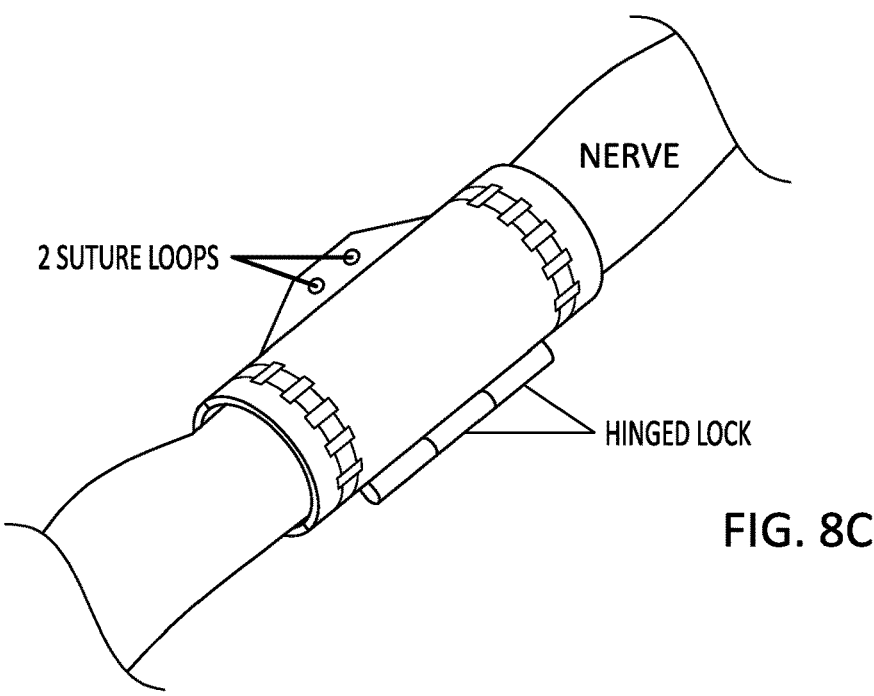

Although in general, the nerve cuff electrodes described herein are similar to those shown in FIGS. 2B-3D, any appropriate nerve cuff electrode may be used. FIGS. 8A-8C illustrate another variation of a nerve cuff electrode in which two halve or sides of the nerve cuff electrode are hinged together and may be coupled over and around a nerve root. For example, in FIG. 8A, the nerve cuff electrode shows a left side 803 and a right side 803' that are joined initially by hinge region 805. The electrodes within the nerve cuff electrode may be similar to those described above, and each half may be connected to a lead 807, 807'. FIG. 8B shows the nerve cuff electrode of FIG. 8A extended over a nerve, and secured on the opposite side by, e.g., a suture. FIG. 8C shows the nerve cuff electrode of FIG. 8A in a perspective view over a nerve.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of minimally invasively attaching a nerve cuff electrode to a patient's nerve root, the method comprising:
    inserting a cannula into the patient's tissue to a nerve root region;
    advancing a nerve cuff deployment tool distally through the cannula to the nerve root region, wherein the nerve cuff electrode is removably attached at a distal end of the nerve cuff deployment tool, wherein the nerve cuff electrode is self-curling or hinged to wrap around the patient's nerve root;
    disengaging the nerve cuff electrode from the nerve cuff deployment tool and causing the nerve cuff electrode to wrap around the patient's nerve root; and
    securing the nerve cuff electrode to the patient's nerve root by looping a suture through suture holes in two regions of the nerve cuff electrode, wherein the suture holds the two regions together around the patient's nerve root.

2. The method of claim 1, wherein the nerve cuff deployment tool includes an elongated body having a column strength sufficient to resist buckling at compressive forces of at least 10 N.

3. The method of claim 1, wherein the nerve cuff electrode includes a self-curling sheet held in an inverted configuration within the nerve cuff deployment tool, wherein the nerve cuff electrode is biased to wrap itself around the patient's nerve root when released from the nerve cuff deployment tool.

4. The method of claim 1, wherein causing the nerve cuff electrode to wrap around the patient's nerve root includes manipulating the nerve cuff electrode to position the nerve cuff electrode around the patient's nerve root.

5. The method of claim 1, wherein the nerve cuff deployment tool is flexible and has a column strength sufficient to resist buckling at compressive forces of at least 10 N.

6. The method of claim 1, wherein the nerve cuff deployment tool includes a bifurcated end that engages with the nerve cuff electrode, wherein disengaging the nerve cuff electrode from the nerve cuff deployment tool includes pushing or pulling the nerve cuff electrode within the cannula.

7. The method of claim 1, wherein the nerve cuff deployment tool includes a hollow member that receives a lead connected to the nerve cuff electrode.

8. The method of claim 1, wherein the nerve cuff deployment tool includes a hinged distal end that is controllable to release the nerve cuff electrode.

9. The method of claim 1, wherein the nerve cuff electrode includes two halves joined by a hinge, wherein securing the nerve cuff electrode to the patient's nerve root comprises securing the two halves using the suture.

10. A nerve cuff deployment system for minimally invasively attaching a nerve cuff electrode to a patient's nerve root, the system comprising:
the nerve cuff electrode, wherein the nerve cuff electrode is self-curling or hinged to wrap around the patient's nerve root, wherein the nerve cuff electrode includes two regions comprising suture holes, wherein the suture holes are arranged to loop a suture therethrough so that the suture can hold the two regions together around the patient's nerve root; and
a nerve cuff deployment apparatus comprising:
an elongated body; and
a nerve cuff engagement region at a distal end of elongated body, the nerve cuff engagement region configured to secure to the nerve cuff electrode and to release the nerve cuff electrode near the patient's nerve root.

11. The system of claim 10, wherein the nerve cuff engagement region comprises a two-part capsule configured to at least partially enclose the nerve cuff electrode, the two-part capsule configured to separate or open for deployment of the nerve cuff electrode.

12. The system of claim 10, wherein the nerve cuff engagement region is configured to hold a self-curling sheet in an inverted configuration, and to release the nerve cuff electrode such that the self-curling sheet wraps itself around the patient's nerve root.

13. The system of claim 10, wherein the nerve cuff engagement region comprises a hook or fork configured to releasably engage with the nerve cuff electrode.

14. The system of claim 10, wherein the nerve cuff engagement region comprises a rounded distal end configured to engage with the nerve cuff electrode.

15. The system of claim 10, further comprising a pusher extending adjacent to the elongated body, the pusher having a distal end configured to apply distal force to the nerve cuff electrode.

16. The system of claim 10, further comprising a proximal control coupled to the elongated body and configured to disengage the nerve cuff engagement region from the nerve cuff electrode.

17. The system of claim 10, wherein the elongated body is flexible and has a column strength sufficient to resist buckling at compressive forces of at least 10 N.

18. A nerve cuff electrode for attaching to a patient's nerve root, the nerve cuff electrode comprising:
a nerve cuff body comprising:
a first half and a second half joined by a hinge, wherein the hinge is configured to transition the first and second halves between an open state and a closed state, wherein when in the closed state, the first and second halves are configured to encircle the patient's nerve root, wherein each of the first and second halves includes a region comprising suture holes, wherein the suture holes are arranged to loop a suture therethrough so that the suture can hold the first and second halves together in the closed state;
a first lead coupled to and extending longitudinally from the first half of the nerve cuff body; and
a second lead coupled to and extending longitudinally from the second half of the nerve cuff body.

19. The nerve cuff electrode of claim 18, wherein each region of the first and second halves comprising the suture holes is on an outer surface of respective first and second halves.

20. The nerve cuff electrode of claim 19, wherein each region of the first and second halves extends proud with respect on the outer surface of respective first and second halves.

* * * * *